(12) United States Patent
Hintzer et al.

(10) Patent No.: US 8,710,257 B2
(45) Date of Patent: Apr. 29, 2014

(54) METHOD OF PREPARING HIGHLY FLUORINATED CARBOXYLIC ACIDS AND THEIR SALTS

(75) Inventors: Klaus Hintzer, Kastl (DE); Tilman C. Zipplies, Burghausen (DE); Oleg Shyshkov, Burgkirchen (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 13/511,939

(22) PCT Filed: Nov. 18, 2010

(86) PCT No.: PCT/US2010/057141
§ 371 (c)(1),
(2), (4) Date: May 24, 2012

(87) PCT Pub. No.: WO2011/066156
PCT Pub. Date: Jun. 3, 2011

(65) Prior Publication Data
US 2012/0245384 A1    Sep. 27, 2012

(30) Foreign Application Priority Data

Nov. 26, 2009   (GB) .................................. 0920718.4

(51) Int. Cl.
*C07C 69/66*     (2006.01)
*C07C 59/135*    (2006.01)
*C07C 235/06*    (2006.01)

(52) U.S. Cl.
USPC ........................... 560/184; 562/586; 564/209

(58) Field of Classification Search
CPC ...... C07C 51/06; C07C 51/09; C07C 59/135; C07C 231/10
See application file for complete search history.

(56) References Cited

U.S. PATENT DOCUMENTS

2006/0281946 A1   12/2006   Morita et al.
2007/0015864 A1    1/2007   Hintzer et al.

OTHER PUBLICATIONS

Zaragoza Dorwald, Side Reactions in Organic Synthesis, 2005, Wiley-VCH Verlag GmbH & Co. KGaA, Weinheim, Preface. p. IX.*
Friedman, L. "Amidation and aminoalkylation of olefins: Blocking techniques in radical chain reactions", Tet, Letters, No. 7, 1961, pp. 238-240.
Gautier, M. el al., "Synthesis of New fluorinated Amphiphiles by Photoamidation of the corresponding olefins", Journal of Fluorine Chemicals, vol. 44, 1989, pp. 419-432.
Lazerte, J.D. et al., "The Free-Radical Catalyzed Addition of Alcohols and Aldehydes to Perfluorooelefins", Journal of the American Chemical Society, vol. 77, No. 1, Feb. 1, 1955.
Urry, W.H., "Peroxide induced additions of Methyl formate to olefins", Journal of the American Chemical Society, vol. 75, No. 19, 1953, pp. 4876-4877.

* cited by examiner

*Primary Examiner* — Paul A Zucker
(74) *Attorney, Agent, or Firm* — C. Michael Geise

(57) ABSTRACT

A method for preparing highly fluorinated carboxylic acids and theirs salts and the precursors thereof.

12 Claims, No Drawings

METHOD OF PREPARING HIGHLY FLUORINATED CARBOXYLIC ACIDS AND THEIR SALTS

CROSS REFERENCE TO RELATED APPLICATIONS

This application is a national stage filing under 35 U.S.C. 371 of PCT/US2010/057141, filed Nov. 18, 2010, which claims priority to Great Britain Application No. 0920718.4, filed Nov. 26, 2009, the disclosure of which is incorporated by reference in their entirety herein.

FIELD

The present disclosure relates to a method of preparing highly fluorinated carboxylic acids and their salts.

BACKGROUND ART

Highly fluorinated carboxylic acids are useful emulsifiers in the aqueous emulsion polymerization of fluorinated monomers. In the past perfluorinated low molecular weight carboxylic acids of the general formula $CF_3-(CF_2)_n-COO^- M^+$ have been used for this purpose, wherein $M^+$ represents a cation and n represents an integer between 4 and 8. However, alternative fluorinated emulsifiers that are more readily degradable have become of interest for various reasons.

Fluorinated polyether carboxylic acids and partially fluorinated carboxylic acids have been suggested as alternative emulsifiers. In particular highly fluorinated fluoroalkoxy carboxylic acids of the general formula $[R_f-O-L-COO-]_i X_i^+$ described in (US2007/0015937 to Hintzer et al,), wherein L represents an alkylene group or an aliphatic hydrocarbon group, $R_f$ represents a linear partially or fully fluorinated aliphatic group interrupted with one or more oxygen atoms, $X_i^+$ represents a cation having the valence i and i is 1, 2 or 3, have been found to be useful alternatives of the commonly used perfluorinated alkanoic acids.

Various methods have been described to prepare these highly fluorinated carboxylic acids. For example, (U.S. patent application Ser. No. 2006/0281946 to Morita et al) describes a process based on a ring opening reaction of tetrafluorooxetanes to create acid fluorides which are then converted into carboxylic acids. However, this process is cumbersome and involves various reaction steps. U.S. patent application Ser. No. 2007/0025902 to Hintzer et al describes the preparation of fluorinated carboxylic acids starting from alcohols, using strong oxidizing agents, such as $RuO_4$, $OsO_4$, permanganates or chromium (VI) oxides. While this reaction can be carried out in an industrial scale with good yields, the heavy metal residues originating from the oxidizing agents have to be retained for environmental reasons making this process expensive. Therefore, there is a need for an alternative process for making highly fluorinated carboxylic acids.

SUMMARY

The inventors have found that fluorinated carboxylic acids may be easily prepared by the radical addition of derivatives of formic acid to fluorinated olefins followed by hydrolysis of the resulting adduct. The reaction can be carried out as a one-pot reaction. The methods provided herein do not require the use of heavy metals and are thus environmentally friendly. The methods provided herein yield the acids in good yields even at moderate temperatures and are thus also economical.

Therefore, in the following there is provided a method for preparing highly fluorinated carboxylic acids and their salts and the precursors thereof comprising subjecting a highly fluorinated olefin of the general formula (I):

to a derivative of formic acid according to the general formula (II):

HCOR (II)

in the presence of a radical initiator and activating the radical initiator to form an O-ester, S-ester or an amide adduct of the general formula (III):

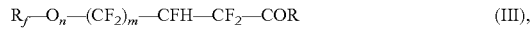

and, optionally, in case the acid is to obtained, hydrolysing the adduct of formula (III) to form the carboxylic acid or its salt of the general formula (IV):

wherein in formulae (II) and (III) R represents a residue $O^-M^+$, $S^-M^+$, OR', SR' or NR'R'' wherein R' and R'' are independent of each other linear or branched or cyclic aliphatic or aromatic residues that contain at least one carbon atom and that do not have an alpha-H-atom and wherein in formulae (I), (III) and (IV) $R_f$ represents H or a perfluorinated or partially fluorinated, linear, branched, aliphatic or aromatic, carbon atoms containing residue and n is either 1 or 0 and m represents an integer between 0 and 6 and $M^+$ represents a cation including $H^+$.

DETAILED DESCRIPTION OF THE INVENTION

Before any embodiments of this disclosure are explained in detail, it is to be understood that the disclosure is not limited in its application to the details set forth in the following description. The invention is capable of other embodiments and of being practiced or of being carried out in various ways.

Also, it is to be understood that the phraseology and terminology used herein is for the purpose of description and should not be regarded as limiting. Contrary to the use of "consisting", which is meant to be limiting, the use of "including," "containing", "comprising," or "having" and is not meant to be limiting and is meant to encompass the items listed thereafter (and equivalents thereof) as well as additional items. The word "consisting" is used to mean the items listed thereafter (and equivalents thereof) but not any additional items. The use of "a" or "an" is meant to encompass "one or more".

Any numerical range recited herein is intended to be an abbreviation and to explicitly include all values from the lower value to the upper value of that range. For example, a concentration range of from 1% to 50% is intended to be an abbreviation and to expressly disclose the values between the 1% and 50%, such as, for example, 2%, 40%, 10%, 30%, 1.5%, 3.9% and so forth.

The methods provided herein allow for the synthesis of fluorinated carboxylic acids of the general formula (IV):

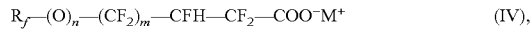

wherein n represents 1 or 0, m represents an integer from 0 to 6 (such as 1, 2, 3, 4, 5 and 6) and $R_f$ represents a perfluorinated or partially fluorinated, linear, branched, aliphatic or aromatic carbon atoms containing residue or represents H. By the term "perfluorinated" is meant that all hydrogen atoms of the residue are replaced by fluorine atoms. For example, the residues $F_3C-$ or $F_3C-O-$ are perfluoromethyl or perfluoromethoxy residues. Typically $R_f$ represents a linear or branched alkyl residue that may contain one or more catenary oxygen atoms. Catenary oxygen atoms are oxygen atoms interrupting the carbon-carbon chain of the alkyl residue.

Examples for $R_f$ include, but are not limited to, perfluorinated alkyl, perfluorinated oxoalkyl, perfluorinated polyoxyalkyl, partially fluorinated alkyl, partially fluorinated oxoalkyl, partially fluorinated polyoxyalkyl residues, which may be linear, cyclic or branched. Typically $R_f$ may contain from 1 to 14 carbon atoms. Specific examples of $R_f$ include but are not limited to $F_3C-$, $F_3CO-$, $F_3CFHC-$, $F_5C_2-$, $F_3COF_2C-$, $F_3COF_2CO-$, $F_7C_3-$, $F_9C_4-$, $F_{11}C_5-$, $F_2HC-$. Further examples include the residues $R_f'-O-(CF_2)_{n'}-$,
$R_f'-(CF_2)_{n'}-$;
$R_f'-(O-CF_2)_{n'}-$,
$R_f'-(O_{CF2}-CF_2)_{n'}-$;
$R_f'-(O-CF_2CF(CF_3))_{n'}-$;
$R_f'-(O-CF(CF_3)-CF_2)_{n'}-$ wherein $R_f'$ is H or a fluorinated or perfluorinated, linear or branched alkyl residue having from 1 to 12 carbon atoms and no or one or more than one catenary oxygen atoms and wherein n' represents 1, 2, 3, 4, 5, 6, 7, 8, 9 or 10.

Preferably $R_f'$ is $F_3C-$, $F_3COF_2C-$, $F_7C_3-$, $F_9C_4-$, $F_{11}C_5-$.

$M^+$ in formula (IV) represents $H^+$ (in case of the free acid) or a cation, such as for example but not limited to metal cations or organic cations (in case of the acid being in the form of its salt). Metal cations include, but are not limited to, $Na^+$ and $K^+$. Organic cations include but are not limited to ammonium ($NH_4^+$), alkylammoniums, alkylphosphoniums and the like.

These acids or their salts may be obtained by a radical addition of a derivative of formic acid to a fluorinated olefin or olefinic ether of the general formula (I):

$$R_f-(O)_n-(CF_2)_m-CF=CF_2 \quad (I)$$

In formula (I) n, m and $R_f$ have the same meaning as described above with respect to formula (IV). It is understood that these units do not change during the reaction and thus, the selection of $R_f$, n and m of the starting material (I) are the same in the final product (IV).

The formic acid derivatives are those wherein the OH group of formic acid (HCOOH) has been replaced by a group R. Therefore, the derivatives of formic acid can be represented by the general formula $$HCOR \quad (II).$$

It is understood that in formula (II) CO represents a carbonyl group and not an ether group. The group R in formula (II) represents $O^-M^+$, $S^-M^+$, OR', SR' and NR'R'' groups wherein $M^+$ represents a cation as defined above with respect for $M^+$ in formula (IV). R' and R'' may be identical or different and represent, independent from each other, a linear, cyclic or branched aromatic or aliphatic residue that contains at least one carbon atom and wherein the residue does not have an alpha-H-atom. An alpha-H-atom is an H atom that is bonded to the carbon atom that is bonded to the O, N, or S atom in the groups OR', SR' and NR'R'', respectively.

The residues R' and R'' are preferably branched alkyl groups, such as, for example, tert-butyl (tBu), isopropyl (iPr) or adamantyl groups, or substituted alkyl groups, such as halogen alkyls, alkoxy alkyls, sulfonyl alkyls or combinations thereof, such as for example, but not limited to $-CCl_3$, $-SO_2-R'''$, wherein R''' is an alkyl (such as, for example, a tert-butyl or a halogenalkyl group (such as, for example, a $CF_3$ group). Preferred examples of R include $-O-tBu$, $-O-iPr$, $-O-adamantyl$, $-O-CCl_3$, $-O-SO_2CF_3$, $-O-SO_2-OtBu$, $-O^-Na^+$ and $-O^-K^+$ To achieve the radical addition a radical initiator is added to the starting materials. Suitable radical initiators are compounds that decompose to generate radicals. The decomposition may be initiated, for example, thermally or by IR- or UV-irradiation or actinic irradiation as known in the art.

Useful radical initiators or photoinitiators include, for example, those known as being useful in actinic radiation or e-beam radiation to cross-link compositions comprising ethylenically unsaturated monomers. Such initiators include benzophenone and its derivatives; benzoin, alpha-methylbenzoin, alpha-phenylbenzoin, alpha-allylbenzoin, alpha-benzylbenzoin; benzoin ethers such as benzil dimethyl ketal (commercially available under the trade designation "IRGACURE™ 651" from Ciba Specialty Chemicals Corporation of Tarrytown, N.Y.), benzoin methyl ether, benzoin ethyl ether, benzoin n-butyl ether; acetophenone and its derivatives such as 2-hydroxy-2-methyl-1-phenyl-1-propanone (commercially available under the trade designation "DAROCUR™ 1173" from Ciba Specialty Chemicals Corporation) and 1-hydroxycyclohexyl phenyl ketone (commercially available under the trade designation "IRGACURE™ 184", also from Ciba Specialty Chemicals Corporation); 2-methyl-1-[4-(methylthio)phenyl]-2-(4-morpholinyl)-1-propanone commercially available under the trade designation "IRGACURE™ 907", also from Ciba Specialty Chemicals Corporation); 2-benzyl-2-(dimethylamino)-1-[4-(4-morpholinyl)phenyl]-1-butanone commercially available under the trade designation "IRGACURE™ 369" from Ciba Specialty Chemicals Corporation); aromatic ketones such as benzophenone and its derivatives and anthraquinone and its derivatives; onium salts such as diazonium salts, iodonium salts, sulfonium salts; titanium complexes such as, for example, that which is commercially available under the trade designation "CGI™ 784 DC", also from Ciba Specialty Chemicals Corporation); halomethylnitrobenzenes; and mono- and bis-acylphosphines such as those available from Ciba Specialty Chemicals Corporation under the trade designations "IRGACURE™ 1700", "IRGACURE™ 1800", "IRGACURE™ 1850","IRGACURE™ 819" "IRGACURE™ 2005", "IRGACURE™ 2010", "IRGACURE™ 2020" and "DAROCUR™ 4265". Combinations of two or more photoinitiators may be used. Examples include a mixture of benzophenone with Irgacure™184, commercially available under the trade designation "IRGACURE™ 500".

Useful thermal initiators include azo compounds, such as azobisisobutyronitrile (AIBN), azo-2-cyanovaleric acid and the like, hydroperoxides such as cumene, t-butyl and t-amyl hydroperoxide, dialkyl peroxides such as di-t-butyl and dicumylperoxide, peroxyesters such as t-butylperbenzoate and di-t-butylperoxy phthalate, t-amyl peroxypivalates, diacylperoxides such as benzoyl peroxide and lauroyl peroxide. Preferred initiators are thermal initiators and of those initiators are preferred which can be activated (i.e. that decompose to form a radical) at moderate temperatures, preferably at a temperature between about 40° C. and about 100° C.

The radical action can also be initiated electrochemically, for example in an electrochemical cell in which case the radicals are generated by high voltage. The initiators may also be chemical radicals or redox system, such as for example nitroxide radicals like TEMPO.

The amount of radical initiator used will depend on the particular reaction. Generally, suitable initiator concentrations are typically from about 0.5 to about 40%, preferably about 5 to 15% by mole with respect to the unsaturated ether. The radical initiators may be added at once, continuously or discontinuously for example at multiple times over a certain time period. Instead of a single initiator a combination of initiators may be used or different initiators may be used at different times.

The formic acid derivatives are typically used in molar excess with respect to the unsaturated ether. Generally, the derivatives are employed in 3 to 5 fold molar excess. In cases where the derivatives are used both as reactants and solvent the molar excess may be much larger.

The addition reaction may be carried out without requiring a solvent although solvents may also be used. Typical solvents include polar organic solvents and/or water and combinations thereof. Suitable solvents include, for example, acetonitrile, DMSO, DMF and the like may be used including mixtures thereof with water. A ratio of water to water miscible solvent (for example $H_2O$:acetonitrile) of 1:1 to 4:1, preferably 1.5:1, based on volume has been found to be suitable. It is also contemplated that the reaction may be carried out using supercritical media (for example sc-$CO_2$) or ionic liquids.

The reaction conditions are chosen depending on the type of initiator used and should ensure that the radical initiator is activated. Once activated the reaction is typically run at moderate temperatures, typically between 30° C. and 100° C. Preferably, radical initiators are employed that can be thermally activated between 30° C. and 100° C. to keep the energy costs low. The reaction times typically involve between 6 to 24 hours. The reaction may be carried out at ambient or increased pressures, for example when gaseous olefins are to be used as reactants The radical addition of the formic acid derivative to the unsaturated fluorinated ether leads to carboxylic acid precursors. Depending on the type of formic acid derivative used the precursor may be an (oxygen) ester, a thioester or an amide.

Generally, the precursors correspond to the general formula

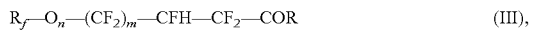

$$R_f\text{—}O_n\text{—}(CF_2)_m\text{—}CFH\text{—}CF_2\text{—}COR \qquad (III),$$

wherein n, m and $R_f$ are defined as described above. It is understood that $R_f$, n and m used in the starting compounds (the unsaturated ethers) will remain the same throughout the reaction.

The precursors may be isolated by known methods of preparative chemistry, such as for example, distillation. Typically, the precursors are directly converted into carboxylic acids or their corresponding salts without isolating them by hydrolysing them in the reaction mixture. This can be typically achieved by adding a base. Typically, aqueous solutions of bases such as sodium or potassium hydroxide may be used.

The resulting acids may be isolated by bringing the acid into its free acid form (by sufficiently lowering the pH if necessary), separating the acid formed from the aqueous phase and purifying them by distillation. One can also extract the acids with water immiscible organic solvents.

The esters formed as reaction products may be also separated from the reaction media by fractional distillation. An advantage of the presently disclosed reaction is that it can be carried out as a one-pot reaction. The methods provided herein do not require the use of heavy metals and are thus environmentally friendly. The methods provided herein yield the acids in good yields, such as yields greater than 50%, greater than 70% or even greater than 80% (based on the molar amount of olefin used as reactant). Such yields may be obtained even at moderate temperatures (e.g. between 30° C. and 100° C.).

The following examples are provided to further illustrate the invention but are not meant to be limiting in any way.

EXAMPLES

Reagents and Chemicals

TAPPI-75-AL=t-amyl peroxypivalate 75%-solution in aliphatics (CAS No. 029240-17-3;
(Degussa Initiators, Pullach, Germany: Trigonox 125-C75, Produkt-Code 436321).

PERKADOX 16S=96% di(4-tert-buthylcyclohexyl)peroxydicarbonate (CAS No. 015520-11-3; Akzo Nobel; Produkt-Code 661041).

TRIGONOX 21S=99% tert-butylperoxy-2-ethylhexanoate (CAS No. 003006-82-4; Akzo Nobel; Produkt-Code 658151).

MV-31=1,1,2,2,3,3-hexafluoro-1-trifluoromethoxy-3-trifluorovinyloxy-propane (Dyneon GmbH, Burgkirchen).

MA-31=1,1,2,3,3-pentafluoro-3-[1,1,2,2,3,3-hexafluoro-3-(trifluoromethoxy)propoxy]prop-1-ene (Dynon GmbH, Burgkirchen).

DONA=2,2,3-trifluoro-3-[1,1,2,2,3,3-hexafluoro-3-(trifluoromethoxy)propoxy]propanoic acid (Dneon GmbH, Burgkirchen).

t-Butyl Formate (CAS No. 762-75-4; Fluka, Cat. No. 06513).

Sodium Formate (CAS No. 141-53-7; Sigma-Aldrich 71541).

Measurements $^1$H-NMR measurements were carried out on Bruker DPX 200 MHz, operating at 200.13 MHz for $^1$H NMR (TMS) and 188.31 MHz for $^{19}$F NMR ($CFCl_3$)

Example 1 tert-butyl 2,2,3-trifluoro-3-[1,1,2,2,3,3-hexafluoro-3-(trifluoromethoxy)propoxy]propanoate
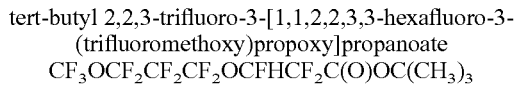
$CF_3OCF_2CF_2CF_2OCFHCF_2C(O)OC(CH_3)_3$ 24.90 g (75 mmol) of MV-31 were mixed with 76.57 g (0.75 mol) of t-butyl formate and 3 ml (10.5 mmol) of TAPPI-75-AL. The mixture was stirred for 18 h at 60° C. Then t-butyl formate was distilled from the reaction mixture using 200 mm Vigreaux column and the raw product was distilled in vacuum to give 23.90 g (55.05 mmol) of a clear colourless liquid; b.p=94-96° C.@75 mmHg. Yield 73%.

Example 2 tert-butyl 2,2,3-trifluoro-3-[1,1,2,2,3,3-hexafluoro-3-(trifluoromethoxy)propoxy]propanoate
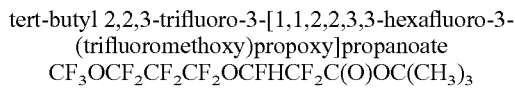
$CF_3OCF_2CF_2CF_2OCFHCF_2C(O)OC(CH_3)_3$ 108.37 g (0.33 mol) of MV-31 were mixed with 200 g (1.96 mol) of t-butyl formate and 13 g (32.6 mmol) of Perkadox 16S. The mixture was stirred for 24 h at 52-55° C. Then t-butyl formate was distilled from the reaction mixture and the raw product was distilled in vacuum to give 131.25 g (0.3 mol) of the clear colourless liquid. Yield 93%.

Example 3 tert-butyl 2,2,3,4,4-pentafluoro-4-[1,1,2,2,3,3-hexafluoro-3-(trifluoromethoxy)propoxy]butanoate
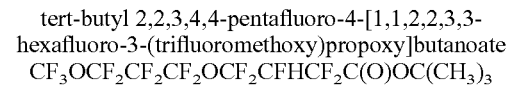
$CF_3OCF_2CF_2CF_2OCF_2CFHCF_2C(O)OC(CH_3)_3$ 18 g (47 mmol) of MA-31 were mixed with 25.1 g (0.25 mol) of t-butyl formate and 2 g (5 mmol) of Perkadox 16S.

The mixture was stirred for 17 h at 55-58° C. Then additional 2 g (5 mmol) of Perkadox 16S were added and the reaction mixture was stirred in the same temperature range for another 15 h. t-Butyl formate was distilled from the reaction mixture and the raw product was distilled in vacuum to give 18.94 g (39.12 mmol) of the clear colourless liquid; b.p=102° C.@75 mmHg. Only traces of the corresponding iso-derivative, see in the example 6, were to be found in the product obtained. Yield 83%.

Example 4

2,2,3-Trifluoro-3-(1,1,2,2,3,3-hexafluoro-3-trifluoromethoxy-propoxy)-propionic acid
$CF_3OCF_2CF_2CF_2OCFHCF_2C(O)OH$ To a solution of 37.1 g (0.54 mol) of sodium formate in the mixture consisting of 200 ml deionised water and 150 ml acetonitrile, 60.2 g (181.30 mmol) of MV-31 and 8 ml (28 mmol) TAPPI-75-AL were added. The mixture was stirred for 18 h at 54-58° C. under reflux with the temperature of reaction mixture rising with formation of the product; the additional 8 ml of TAPPI-75-AL and the reaction mixture was stirred at 58-65° C. for 16 h. The reaction mixture was acidified with sulphuric acid till pH=1 and the bottom phase formed was separated and washed with 10% solution of sulphuric acid three times (3×100 ml). The crude product was distilled in vacuum to give 58.82 g (155.30 mol) of the acid; b.p.=87.7° C.@15 mmHg. Yield 85%.

Example 5

2,2,3-Trifluoro-3-(1,1,2,2,3,3-hexafluoro-3-trifluoromethoxy-propoxy)-propionic acid
$CF_3OCF_2CF_2CF_2OCFHCF_2C(O)OH$ The reaction described in the example 4 was repeated with using Trigonox 21S (2×8 gr, 74 mmol) as a radical initiator instead of TAPPI-75-AL. The Trigonox 21S was added in two portions at the 16 h interval. The reaction temperature did not change significantly during the reaction process and remained between 53-55° C. under the constant reflux. The product formation was followed by $^{19}F$ NMR.

Example 6

2,2,3,4,4-pentafluoro-4-[1,1,2,2,3,3-hexafluoro-3-(trifluoromethoxy)propoxy]butanoic acid
$CF_3OCF_2CF_2CF_2OCF_2CFHCF_2C(O)OH$ {A} and
iso-=$CF_3OCF_2CF_2CF_2OCF_2CF(CF_2H)$—$C(O)OH$ {B}

11 g (162 mmol) of sodium formate were dissolved in the mixture consisting of 67 ml of deionised water and 50 ml of acetonitrile. To the mixture obtained 20.4 g (53.4 mmol) of MA-31 and 6 ml (21 mmol) TAPPI-75-AL were added and the mixture was stirred at 60° C. for 24 h. Reaction products were not isolated. The $^{19}F$ NMR spectra and gas-chromatograms of the reaction mixture revealed nearly quantitative conversion of the starting allyl ether and formation of two acids of isomeric structure: A/B=1.8/1

Example 7

2,2,3-trifluoro-3-[1,1,2,2,3,3-hexafluoro-3-(trifluoromethoxy)propoxy]propanamide
$CF_3OCF_2CF_2CF_2OCFHCF_2C(O)NH_2$ The mixture consisting of 57.32 g (172.63 mmol) of MV-31, 150 ml formamide, 70 ml acetonitrile and 8.53 ml (29.8 mmol) of TAPPI-75-AL was stirred for 18 h at 55-57° C. The formation of the amide was observed by $^{19}F$ NMR spectrometry and gas-chromatography.

The invention claimed is:

1. A method for preparing highly fluorinated carboxylic acids and theirs salts and the precursors thereof comprising subjecting a highly fluorinated olefin of the general formula (I):

$$R_f—(O)_n—(CF_2)_m—CF=CF_2 \quad (I)$$

to a derivative of formic acid according to the general formula (II):

$$HCOR \quad (II)$$

in the presence of a radical initiator and activating the initiator to form carboxylic acid precursor in the form of an O-ester, S-ester or an amide adduct of the general formula (III):

$$R_f—O_n—(CF_2)_m—CFH—CF_2—COR \quad (III),$$

and optionally, in case the acid is to be obtained, hydrolysing the adduct of formula (III) to form the carboxylic acid or its salt of the general formula (IV):

$$R_f—O_n—(CF_2)_m—CFH—CF_2—COO^-M^+ \quad (IV),$$

wherein in formulae (II) and (III) R represents a residue $O^-M^+$, $S^-M^+$, OR', SR' or NR'R" wherein R' and R" are independent of each other linear or branched or cyclic aliphatic or aromatic residues that contain at least one carbon atom and that do not have an alpha-H-atom and wherein in formulae (I), (III) and (IV) $R_f$ represents H or a perfluorinated or partially fluorinated, linear, branched, aliphatic or aromatic, carbon atoms containing residue and n is either 1 or 0 and m represents an integer between 0 and 6 and $M^+$ represents a cation including $H^+$.

2. The method according to claim 1 wherein $R_f$ represents a fluorinated or perfluorinated, linear or branched alkyl residue that may contain one or more catenary oxygen atoms.

3. The method according to claim 1 wherein $R_f$ represents one of the following:
$R_{f'}—O—(CF_2)_{n'}—$,
$R_{f'}—(CF_2)_{n'}—$,
$R_{f'}—(O—CF_2)_{n'}—$,
$R_{f'}—(O—CF_2—CF_2)_{n'}—$,
$R_{f'}—(O—CF_2CF(CF_3))_{n'}—$,
$R_{f'}—(O—CF(CF_3)—CF_2)_{n'}—$
wherein $R_{f'}$ is a fluorinated or perfluorinated alkyl residue having from 1 to 12 carbon atoms and no or one or more than one catenary oxygen atoms and wherein n' represents 1, 2, 3, 4, 5, 6, 7, 8, 9 or 10.

4. The method according to claim 1 wherein $R_f$ contains from 1 to 12carbon atoms.

5. The method according to claim 1 wherein R is —OR' and R' is a branched alkyl or a branched halogen alkyl.

6. The method according to claim 1 wherein R is —OR' and R' represents a tert-butyl (tBu), an isopropyl (iPr), an adamantyl groups, —$SO_2CF_3$, —O —$SO_2$-OtBu, —$O^-Na^+$ and —$O^-K^+$.

7. The method according to claim 1 wherein the hydrolysis is carried out by adding a base.

8. The method according to claim 1 wherein the radical initiator is activated thermally.

9. The method according to claim 8 wherein the radical initiator is activated at a temperature between about 30° C. and about 100° C.

10. The method according to claim 1 wherein the highly fluorinated carboxylic acids are obtained in a yield of greater than 50% based on the molar amount of the highly fluorinated olefin used as reactant.

11. The method according to claim 1 wherein the highly fluorinated carboxylic acids are obtained in a yield of greater than 70% based on the molar amount of the highly fluorinated olefin used as reactant.

12. The method according to claim 1 wherein the highly fluorinated carboxylic acids are obtained in a yield of greater than 80% based on the molar amount of the highly fluorinated olefin used as reactant.

* * * * *

UNITED STATES PATENT AND TRADEMARK OFFICE
CERTIFICATE OF CORRECTION

PATENT NO.         : 8,710,257 B2
APPLICATION NO.    : 13/511939
DATED              : April 29, 2014
INVENTOR(S)        : Klaus Hintzer It is certified that error appears in the above-identified patent and that said Letters Patent is hereby corrected as shown below:

On the Title Page:

Column 2
(Other Publications), Line 10, Delete "Perfluorooelefins"," and insert -- Perfluoroolefins", --, therefor.
Item (57), Abstract, Line 2, Delete "theirs" and insert -- their --, therefor.

In the Specification:

Column 3
Line 14, Delete "—(CF$_2$)$_n$—;" and insert -- —(CF$_2$)$_{n'}$—, --, therefor.
Line 16, Delete "R$_{f'}$—(O$_{CF2}$—CF$_2$)$_n$—;" and insert -- R$_{f'}$—(O—CF$_2$—CF2)$_{n'}$—, --, therefor.
Line 17, Delete "(CF$_3$))$_n$—;" and insert -- (CF$_3$))$_{n'}$—, --, therefor.

Column 4
Line 2, After "—O$^-$K$^+$" insert -- . --.
Line 41, Delete "1850","IRGACURE™" and insert -- 1850", "IRGACURE™ --, therefor.
Line 45, Delete "Irgacure™184," and insert -- IRGACURE™ 184, --, therefor.

Column 5
Line 30, After "reactants" insert -- . --.

Column 6
Line 10, Delete "buthylcyclohexyl)" and insert -- butylcyclohexyl) --, therefor.
Line 19, Delete "(Dynon" and insert -- (Dyneon --, therefor.
Line 22, Delete "(Dneon" and insert -- (Dyneon --, therefor.
Line 31, After "(CFCl$_3$)" insert -- . --.
Line 43, Delete "Vigreaux" and insert -- Vigreux --, therefor.

Signed and Sealed this
Fifth Day of August, 2014

Michelle K. Lee
*Deputy Director of the United States Patent and Trademark Office*

CERTIFICATE OF CORRECTION (continued)
U.S. Pat. No. 8,710,257 B2

Column 7
Line 58, After "1.8/1" insert -- . --.

In the Claims:

Column 8
Line 7, In Claim 1, delete "theirs" and insert -- their --, therefor.
Line 54, In Claim 4, delete "12carbon" and insert -- 12 carbon --, therefor.
Line 59, In Claim 6, delete "—O —SO$_2$-OtBu," and insert -- —O—SO$_2$-OtBu, --, therefor.